United States Patent [19]
Zirps et al.

[11] Patent Number: 6,139,214
[45] Date of Patent: Oct. 31, 2000

[54] QUICK DISCONNECT COUPLING FOR SURGICAL INSTRUMENT

[75] Inventors: Christopher Zirps, Milton; William R. Rebh, Shrewsbury; Matthew Emans, Boston, all of Mass.

[73] Assignee: Endius Incorporated, Plainville, Mass.

[21] Appl. No.: 09/211,238

[22] Filed: Dec. 14, 1998

[51] Int. Cl.[7] .................................................. F16B 21/06
[52] U.S. Cl. ...................... 403/325; 403/328; 403/24; 606/170
[58] Field of Search ..................................... 403/325, 324, 403/321, 327, 328, 376, 109.2, 109.8, 24; 285/308, 310; 606/170, 171, 180; 604/22

[56] References Cited

U.S. PATENT DOCUMENTS

| | | | |
|---|---|---|---|
| 4,804,213 | 2/1989 | Guest ....................................... | 285/308 |
| 5,292,329 | 3/1994 | Werner ................................. | 606/170 X |
| 5,374,088 | 12/1994 | Moretti et al. ....................... | 285/308 X |
| 5,380,333 | 1/1995 | Meloul et al. ....................... | 606/170 X |
| 5,452,924 | 9/1995 | Kujawski ............................. | 285/308 X |
| 5,567,047 | 10/1996 | Fritsch ................................. | 403/325 X |
| 5,568,946 | 10/1996 | Jackowski ........................... | 285/308 X |
| 5,681,257 | 10/1997 | Letourneur ........................... | 403/325 X |
| 5,782,836 | 7/1998 | Umber et al. ....................... | 606/180 X |
| 5,810,879 | 9/1998 | De Guillebon ..................... | 606/170 X |

*Primary Examiner*—Harry C. Kim
*Attorney, Agent, or Firm*—Tarolli, Sundheim, Covell, Tummino & Szabo L.L.P.

[57] ABSTRACT

A coupling for releasably connecting first and second parts of an apparatus such as a surgical instrument. The coupling comprises a socket member on the first part of the apparatus, the socket member having an axially extending central opening, and a plug member on the second part of the apparatus. The socket member includes a first manually depressible release button and a first locking element spaced apart from each other on opposite sides of the central opening and movable radially with each other relative to the central opening when the plug member is received in the central opening in the socket member. The first locking element moves away from the central opening when the first release button is depressed. The socket member also includes a second manually depressible release button and a second locking element spaced apart from each other on opposite sides of the central opening and movable radially with each other relative to the central opening when the plug member is received in the central opening in the socket member. The second locking element moves away from the central opening when the second release button is depressed. The first and second locking elements are engageable with the plug member to block axial movement between the plug member and the socket member when the plug member is received in the central opening in the socket member.

16 Claims, 3 Drawing Sheets

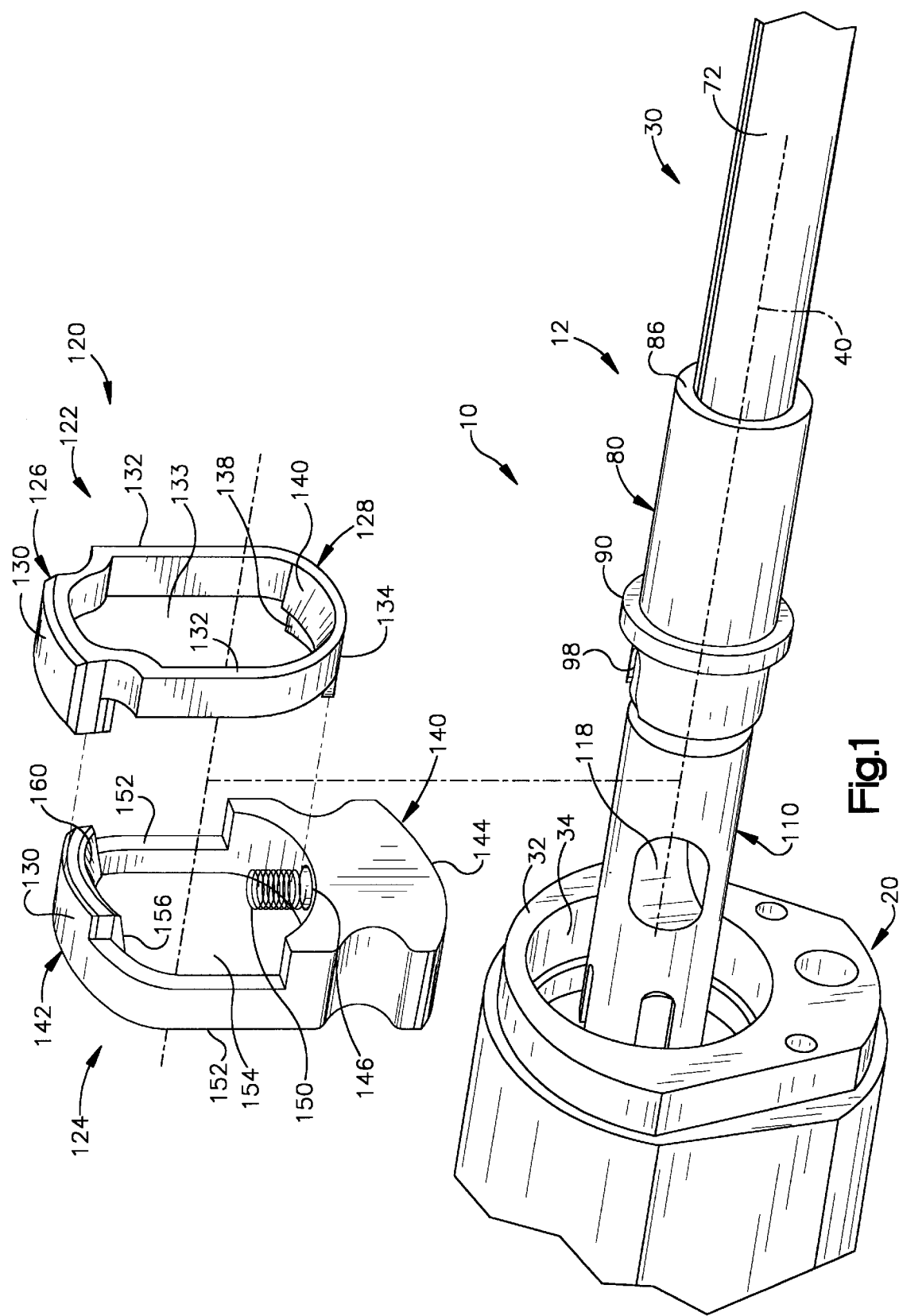

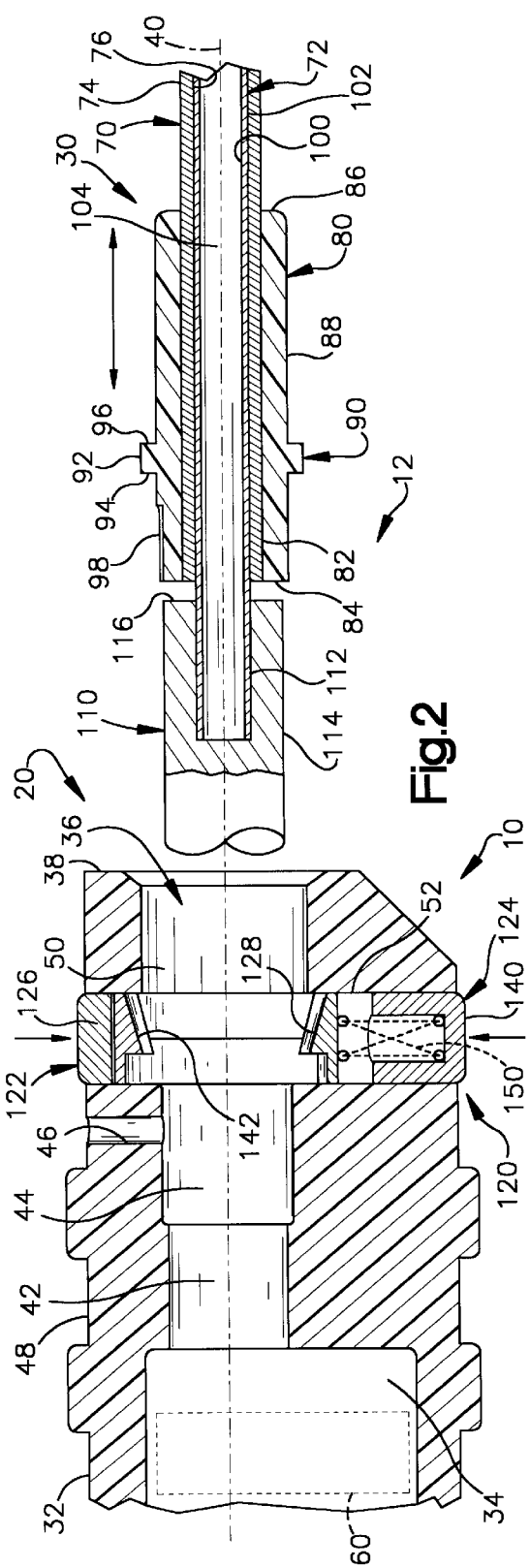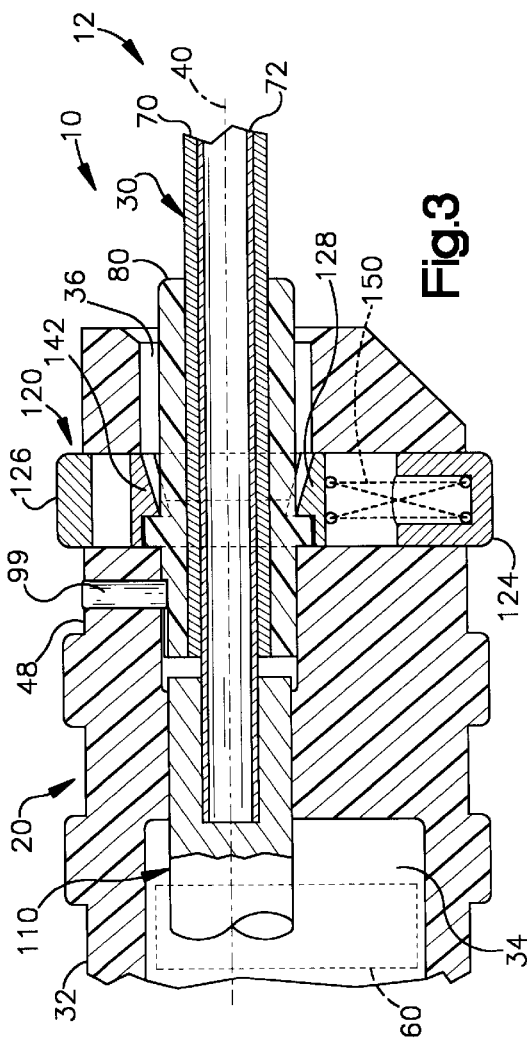

QUICK DISCONNECT COUPLING FOR SURGICAL INSTRUMENT

BACKGROUND OF THE INVENTION

The present invention relates to a coupling for joining two parts of a device. In particular, the present invention relates to a quick disconnect coupling for releasably joining a base or handle portion of a surgical instrument with a disposable working portion of the surgical instrument, such as a shaver or suction tool.

SUMMARY OF THE INVENTION

The present invention is a coupling for releasably connecting first and second parts of an apparatus. The coupling comprises a socket member on the first part of the apparatus, the socket member having an axially extending central opening. A plug member on the second part of the apparatus is to be received coaxially in the central opening in the socket member. A first one of the plug member and the socket member includes a first manually depressible release button and a first locking element spaced apart from each other on opposite sides of the central opening and movable radially with each other relative to the central opening when the plug member is received in the central opening in the socket member. The first locking element moves away from the central opening when the first release button is depressed. The first one of the plug member and the socket member also includes a second manually depressible release button and a second locking element spaced apart from each other on opposite sides of the central opening and movable radially with each other relative to the central opening when the plug member is received in the central opening in the socket member. The second locking element moves away from the central opening when the second release button is depressed. The first and second locking elements are engageable with the second one of the plug member and the socket member to block axial movement between the plug member and the socket member when the plug member is received in the central opening in the socket member.

In a preferred embodiment, the present invention is a surgical instrument comprising a first part and a second part releasably connectable with the first part. The first part of the surgical instrument includes a socket member having an axially extending central opening. The second part of the surgical instrument includes a plug member to be received coaxially in the central opening in the socket member. The socket member includes a first manually depressible release button and a first locking element spaced apart from each other on opposite sides of the central opening and movable radially with each other relative to the central opening when the plug member is received in the central opening in the socket member. The first locking element moves away from the central opening when the first release button is depressed. The socket member also includes a second manually depressible release button and a second locking element spaced apart from each other on opposite sides of the central opening and movable radially with each other relative to the central opening when the plug member is received in the central opening in the socket member. The second locking element moves away from the central opening when the second release button is depressed. The first and second locking elements are engageable with the plug member to block axial movement between the plug member and the socket member when the plug member is received in the central opening in the socket member.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is a partial perspective view of a surgical instrument including a coupling constructed in accordance with the present invention;

FIG. 2 is a sectional view through the surgical instrument of FIG. 1, showing the parts of the surgical instrument in a disengaged or uncoupled condition FIG. 3 is a view similar to FIG. 2 showing the parts of the surgical instrument in an engaged or coupled condition.

DESCRIPTION OF A PREFERRED EMBODIMENT

Figure 4:
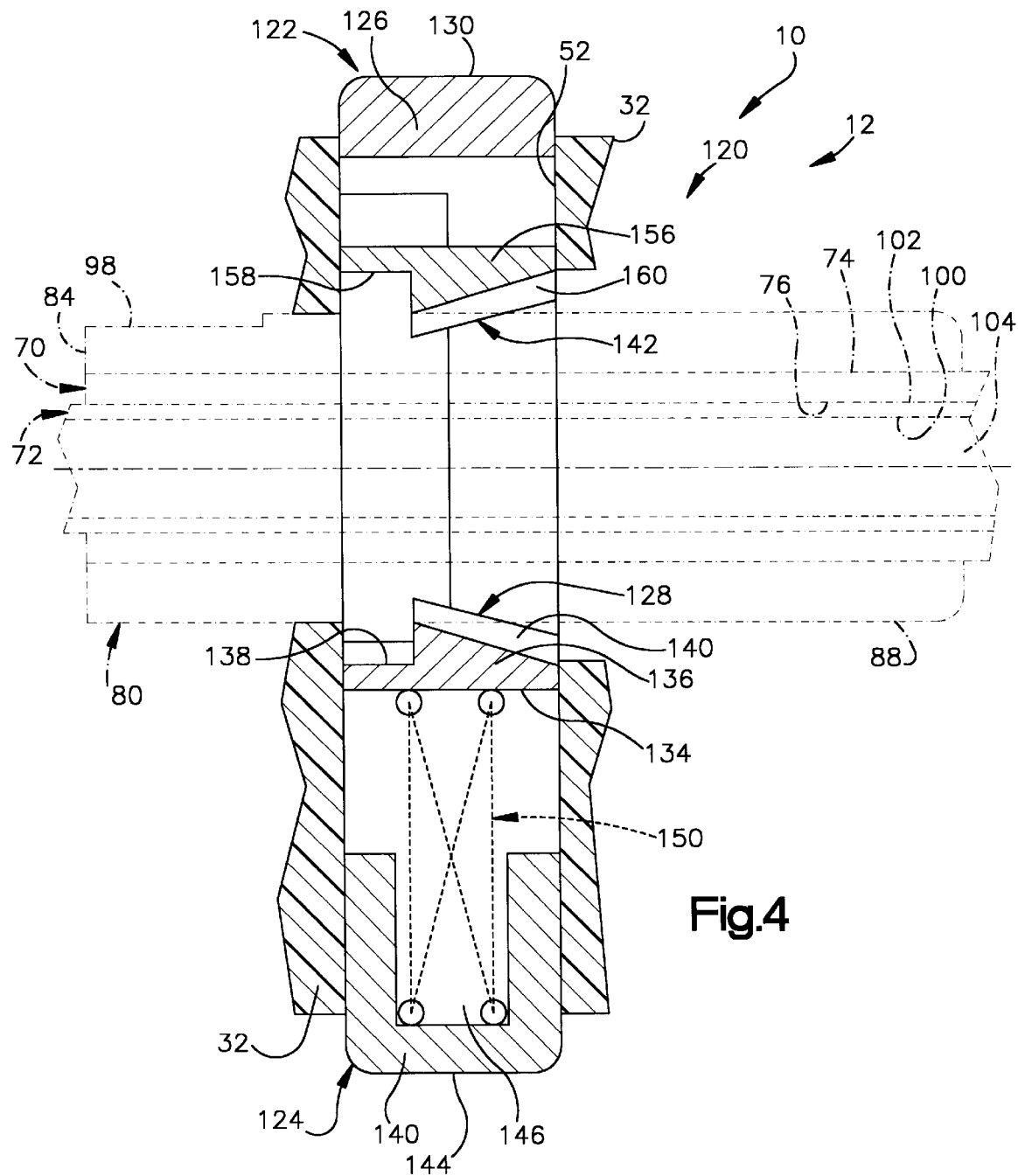
FIG. 4 is an enlarge sectional view of a locking assembly which forms part of the surgical instrument of FIG. 1.

The present invention relates to a quick disconnect coupling for joining two parts of a device, such as a surgical instrument. As representative of the present invention, FIG. 1 illustrates a coupling 10 which forms part of a surgical instrument 12.

The surgical instrument 12 includes a first part 20 and a second part 30. The first part 20 of the surgical instrument 12, a base or handle portion, is a reusable or permanent part of the surgical instrument. The second part 30 of the surgical instrument 12 is a disposable part of the surgical instrument. The second part 30 of the surgical instrument 12 is releasably connectable with the first part 20 in a manner described below.

The first part 20 of the surgical instrument 12 includes a socket member or handle 32. A motor chamber 34 is formed in the handle assembly 32.

The first part 20 includes a central opening in the form of a generally cylindrical insertion passage or socket 36. The insertion passage 36 extends between a distal end face 38 of the handle 32 and the motor chamber 34. The insertion passage 36 is centered on a longitudinal axis 40 of the instrument 12.

A first or proximal portion 42 of the insertion passage 36 communicates directly with the motor chamber 34 and has a first, relatively narrow, cross-sectional diameter. A second portion 44 of the insertion passage 36 extends distally from the first portion 42 and has a slightly larger diameter than the first portion. A locking pin opening 46 extends radially outward from the second portion 44 of the passage 36 to the outer side surface 48 of the handle 32. A third portion 50 of the insertion passage 36 extends distally from the second portion 46 to the distal end face 38 of the handle 32. The outer end of the third portion 50 is beveled to guide insertion of the second part 30 of the instrument into the passage 36.

The handle 32 also includes an opening 52 for receiving a locking assembly 120 described below. An electric drive motor indicated schematically at 60 is disposed in the motor chamber 34. The handle 32 includes parts (not shown) for making electrical connections to the drive motor 60, as well as suction and irrigation connections as desired.

The second part 30 of the surgical instrument 12 is preferably a disposable item such as a suction tool, for example, or shaver. In the illustrated embodiment, the second part 30 of the surgical instrument 12 is a rotary shaver. The proximal end portion of the second part 30 of the instrument part 12 is configured as a plug which is receivable in the socket of the first part 20 of the instrument, in a manner described below.

The second part 30 of the surgical instrument 12 includes coaxial outer and inner tubes 70 and 72. The inner tube 72 is a drive shaft and is rotatably received in the outer tube 70. The outer tube 70 is a metal tube having a cylindrical cross-sectional configuration including parallel, cylindrical inner 74 and outer surfaces 76. A non-rotating outer part of a shaver (not shown) is fixed to the distal end of the outer tube 70.

A locking coupler 80 is fixed to a proximal end portion 82 of the outer tube 70. The locking coupler 80 is a plastic member molded on the outer surface 76 of the outer tube 70. The locking coupler 80 has a generally cylindrical configuration including proximal and distal end faces 84 and 86. The locking coupler 80 has a cylindrical outer surface 88 centered on the axis 40.

An annular locking rib 90 is formed on the locking coupler 80. The locking rib 90 extends circumferentially for 360 degrees around the outer periphery of the locking coupler 80. The locking rib 90 is located near the proximal end 84 of the locking coupler 80. The locking rib 90 has an axially extending, cylindrical outer surface 92 extending between parallel, radially extending side surfaces 94 and 96.

A groove 98 is formed in one side of the locking coupler 80. The groove 98 extends distally from the proximal end face 84 of the locking coupler 80, but does not extend to the locking rib 90. The groove 98 is configured to receives a locking pin 99 as described below to prevent rotation of the outer tube 70 relative to the handle 32.

The drive shaft 72 is a metal tube having parallel, axially extending cylindrical inner and outer surfaces 100 and 102. The drive shaft 72 is rotatable about the axis 40 within the outer tube 70. The cylindrical outer surface 102 of the drive shaft 72 is in sliding engagement with the cylindrical inner surface 74 of the outer tube 70. The cylindrical inner surface 100 of the drive shaft 72 defines a fluid passage 104 in the surgical instrument 12. A rotating inner part of a shaver (not shown) is fixed to the distal end of the drive shaft 72.

A plastic drive coupler 110 is molded on a proximal end portion 112 of the drive shaft 72. The drive coupler 110 has a cylindrical outer side surface 114. A distal end 116 of the drive coupler 110 is spaced axially from the proximal end 84 of the locking coupler 80. A portion of the drive coupler 110 including openings 118 (FIG. 1) is engageable with the electric drive motor 60 to couple the drive shaft 72 to the output of the electric motor.

A locking mechanism 120 is included on the handle 32 for engagement with the locking coupler 80. The locking mechanism 120 is disposed in the opening 52 in the handle 32. The locking mechanism 120 includes a first release member 122 and a second release member 124.

The first release member 122 is made as one piece and includes a first release button 126 and a first locking element 128. The first release button 126 has a manually engageable outer side surface 130. A pair of connecting arms 132 (FIG. 2) extend from the first release button 126 and connect the first release button with the first locking element 128. The first release button 126, first locking element 128, and connecting arms 130 form a closed figure defining an opening 133 extending axially through the first release member 122.

The first locking element 128 has a radially outer side surface 134. The first locking element 128 has a ramp portion 136 and a locking groove 138. The ramp portion 136 has a ramp surface 140 presented radially inward toward the axis 40.

The second release member 124 is generally similar in configuration to the first release member 122 and includes a second release button 140 and a second locking element 142 formed as one piece with each other. The second release button 140 has a manually engageable outer side surface 144. A spring pocket 146 is formed in the second release button 140. A biasing spring 150 is received in the spring pocket 146. The second release button 140 has a larger radial extent than the first release button 126, to accommodate the spring pocket 146.

A pair of connecting arms 152 (FIG. 2) extend from the second release button 140 and connect the second release button with the second locking element 142. The second release button 140, the second locking element 142, and the connecting arms 152 form a closed figure defining an opening 154 extending axially through the second release member 124.

The second locking element 142 has a ramp portion 156 and a locking groove 158. The ramp portion 156 has a ramp surface 160 presented radially inward toward the axis 40.

The release members 122 and 124 are aligned axially with each other. Specifically, the second locking element 142 is disposed radially inward of the first release button 126. The first locking element 128 is disposed radially inward of the second release button 140. The openings 133 and 154 are co-extensive.

The biasing spring 150 extends between the second release button 140 and the radially outer side surface 134 of the first locking element 128. The biasing spring 50 biases the first and second release buttons 126 and 140 relative to each other into a radially outward position as shown in FIG. 3 in which they project from the outer side surface 48 of the handle 32. The first and second locking elements 128 and 142 are spaced apart from each other on opposite sides of the axis 40.

To connect the first part 20 of the surgical instrument with the second part 30, the distal end portion of the second part is inserted into the insertion passage 36 in the handle 32. The drive coupler 110 passes freely through the opening in the distal end face 38 of the handle 32. The drive coupler 110 passes between the locking elements 128 and 142 and into the motor chamber 34. The drive coupler portion including the openings 118 engages parts (not shown) on the output of the drive motor 60. As a result, the drive shaft 72 is coupled for rotation with the output of the drive motor 60.

While the drive shaft 72 is thus being coupled with the drive motor 60, the locking coupler 80 on the outer tube 70 moves into the locking or engaged position shown in FIG. 3. The locking coupler 80 moves into the opening 133 in the first release member 122 and the opening 154 in the second release member 124. The locking rib 90 on the locking coupler 80 move axially into engagement with the ramp surfaces 140 and 160 on the first and second locking elements 128 and 142, respectively. The locking rib 90 forces the locking elements 128 and 142 to move radially outward as it passes axially between them, against the force of the biasing spring 150.

As the locking elements 128 and 142 move radially outward, away from the axis 40, the release buttons 126 and 140 move radially inward, toward the axis. Specifically, as the first locking element 128 moves radially outward, the first release button 126 moves radially inward. As the second locking element 142 moves radially outward, the second release button 140 moves radially inward.

As the second part 30 of the surgical instrument 12 moves farther into position in the first part 20, the locking rib 90 moves past the ramp portions 136 and 156 of the locking elements 128 and 140, and into a position axially aligned with the locking grooves 138 and 158 on the locking elements. The force of the biasing spring 150 causes the release members 122 and 124 to snap into the engaged or locking condition shown in FIGS. 2 and 4. The locking elements 128 and 142 move toward the axis 40, into engagement with the locking coupler 80. The locking rib 90 on the locking coupler 80 is received in the locking grooves 138 and 158. At the same time, the release buttons 124 and 126 move radially outward also, to a position as shown in FIG. 3 in which they project from the outer side surface 48 of the handle 32.

The engagement of the locking rib 90 with the locking elements 128 and 142 prevents axial movement of the second part 30 of the surgical instrument 12 relative to the first part 20, in a distal direction (to the right as viewed in the drawings). Specifically, the one radially extending side surface 96 of the locking rib 90 engages the ramp portions 136 and 156 of the locking elements 128 and 142, respectively. The opposite radially extending side surface 94 of the locking rib 90 engages the handle 32. As a result, the locking rib 90 is captured axially between the locking elements 128 and 142 and the handle 32. The second part 30 of the surgical instrument 12 is thus securely retained in the first part 20. A locking pin 99 inserted into the locking pin passage 46 prevents rotation of the outer tube 70 about the axis 40. The inner tube or drive shaft 72 is rotatable, by the drive motor 60, relative to the outer tube 70, to effect cutting of tissue with the shaver in a known manner.

To release the second part 30 of the surgical instrument 12 from the first part 10, the release buttons 126 and 140 are manually engaged and moved radially inward, against the force of the biasing spring 50. As the first release button 126 moves radially inward, the first locking element 128 moves radially outward, away from the axis 40 and out of engagement with the locking coupler 80. As the second release button 140 moves radially inward, the second locking element 142 moves radially outward, away from the axis 40 and out of engagement with the locking coupler 80. The parts of the locking assembly 120 assume the disengaged or release condition shown in FIG. 4. When the parts of the locking assembly 120 are in this condition, the second part 30 of the surgical instrument 12 can be moved axially out of the insertion passage 36, to disconnect and remove the second part of the surgical instrument from the first part 20.

From the above description of the invention, those skilled in the art will perceive improvements, changes and modifications in the invention. For example, the present invention is applicable to apparatus other then surgical instruments, such as other types of tools, fluid couplings, etc. Such improvements, changes and modifications within the skill of the art are intended to be covered by the appended claims.

Having described the invention, we claim:

1. A coupling for releasably connecting first and second parts of an apparatus, said coupling comprising:
    a socket member on the first part of said apparatus, said socket member having an axially extending central opening; and
    a plug member on the second part of said apparatus, said plug member to be received coaxially in said central opening in said socket member;
    a first one of said plug member and said socket member including a first manually depressible release button and a first locking element spaced apart from each other on opposite sides of said central opening and movable radially with each other relative to said central opening when said plug member is received in said central opening in said socket member, said first locking element moving away from said central opening when said first release button is depressed;
    said first one of said plug member and said socket member also including a second manually depressible release button and a second locking element spaced apart from each other on opposite sides of said central opening and movable radially with each other relative to said central opening when said plug member is received in said central opening in said socket member, said second locking element moving away from said central opening when said second release button is depressed;
    said first and second locking elements being engageable with said second one of said plug member and said socket member to block axial movement between said plug member and said socket member when said plug member is received in said central opening in said socket member.

2. A coupling as set forth in claim 1 wherein said socket member includes said first and second release buttons and said first and second locking elements, and said plug member is engageable with said locking elements on said socket member.

3. A coupling as set forth in claim 2 wherein said first and second release buttons are located diametrically opposite each other on said socket member and said first and second locking elements are located diametrically opposite each other.

4. A coupling as set forth in claim 1 wherein said plug member comprises an annular locking rib which is engageable with said locking elements to block axial movement of said plug member out of said central opening in said socket member.

5. A coupling as set forth in claim 1 wherein said first release button and said first locking element are formed as one piece, said second release button and said second locking element being formed as one piece and being aligned axially with said first release button and said first locking element.

6. A coupling as set forth in claim 5 further comprising a biasing spring which extends between said second release button and said first locking element and which biases said first and second release buttons relative to each other into a radially outward position.

7. A coupling as set forth in claim 1 wherein said first and second locking elements have respective ramp portions which are engageable by said plug member to move said first and second release buttons radially inward in response to movement of said plug member into said socket member.

8. A coupling as set forth in claim 1 wherein said apparatus is a surgical instrument, said first part of said apparatus comprising a base or handle portion of said surgical instrument, said second part of said apparatus comprising a disposable working portion of said surgical instrument.

9. A coupling as set forth in claim 8 wherein said second part of said apparatus comprising a disposable shaver device including first and second relatively rotatable tubes.

10. A coupling as set forth in claim 1 wherein said apparatus is a surgical instrument, said first part of said apparatus comprising a base or handle portion of said surgical instrument, said second part of said apparatus comprising a at least one tubular member having a locking rib engageable with said locking elements.

11. A surgical instrument comprising:
    a first part; and
    a second part releasably connectable with said first part;
    said first part of said surgical instrument including a socket member having an axially extending central opening; and said second part of said surgical instrument including a plug member to be received coaxially in said central opening in said socket member;

said socket member including a first manually depressible release button and a first locking element spaced apart from each other on opposite sides of said central opening and movable radially with each other relative to said central opening when said plug member is received in said central opening in said socket member, said first locking element moving away from said central opening when said first release button is depressed;

said socket member also including a second manually depressible release button and a second locking element spaced apart from each other on opposite sides of said central opening and movable radially with each other relative to said central opening when said plug member is received in said central opening in said socket member, said second locking element moving away from said central opening when said second release button is depressed;

said first and second locking elements being engageable with said plug member to block axial movement between said plug member and said socket member when said plug member is received in said central opening in said socket member.

12. A surgical instrument as set forth in claim 11 wherein said first and second release buttons are located diametrically opposite each other on said socket member and said first and second locking elements are located diametrically opposite each other.

13. A surgical instrument as set forth in claim 12 wherein said plug member comprises an annular locking rib which is engageable with said locking elements to block axial movement of said plug member out of said central opening in said socket member.

14. A surgical instrument as set forth in claim 11 wherein said first release button and said first locking element are formed as one piece, said second release button and said second locking element being formed as one piece and being aligned axially with said first release button and said first locking element.

15. A surgical instrument as set forth in claim 14 further comprising a biasing spring which extends between said second release button and said first locking element and which biases said first and second release buttons relative to each other into a radially outward position.

16. A surgical instrument as set forth in claim 11 wherein said first and second locking elements have respective ramp portions which are engageable by said plug member to move said first and second release buttons radially inward in response to movement of said plug member into said socket member.

* * * * *